US00PP35378P2

(12) United States Plant Patent
Clark et al.

(10) Patent No.: US PP35,378 P2
(45) Date of Patent: Sep. 12, 2023

(54) GRAPE PLANT NAMED 'A-1400'

(50) Latin Name: ***Vitis* L. hybrid**
Varietal Denomination: A-1400

(71) Applicant: THE BOARD OF TRUSTEES OF THE UNIVERSITY OF ARKANSAS, Little Rock, AR (US)

(72) Inventors: John R. Clark, Fayetteville, AR (US); James N. Moore, Arlington, TX (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 17/968,516

(22) Filed: Oct. 18, 2022

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./156, 205, 206, 207
See application file for complete search history.

(56) References Cited

U.S. PATENT DOCUMENTS

| | | | |
|---|---|---|---|
| PP6,159 | P | 4/1988 | Reisch |
| PP13,309 | P2 | 12/2002 | Clark et al. |
| PP25,152 | P3 | 12/2014 | Clark et al. |
| PP25,696 | P3 | 7/2015 | Clark et al. |
| PP25,697 | P3 | 7/2015 | Clark et al. |
| PP25,726 | P3 | 7/2015 | Clark et al. |
| PP25,746 | P3 | 7/2015 | Clark et al. |
| PP30,425 | P3 | 4/2019 | Clark |
| PP30,513 | P3 | 5/2019 | Clark et al. |
| PP31,526 | P2 | 3/2020 | Clark |
| PP34,850 | P2 | 12/2022 | Clark |
| PP34,869 | P2 | 12/2022 | Clark |

OTHER PUBLICATIONS

Scheiner et al. 2022. 'Southern Sensation Seedless' Grape. HortScience 57(2): 345-348. (Year: 2022).*

McWhirt, A.L. et al. Small Fruit Cultivar Recommendations for Arkansas. University of Arkansas System Division of Agriculture. (2021) FSA6130. https://www.uaex.edu/publications/PDF/FSA-6130.pdf.

Scheiner, J., et al. 'Southern Sensation Seedless' Grape. HortScience (2022) 57(2): 345-348.

Stein, L.A. Table Grapes for Texas—Experimental Planting Indicates Exciting Potential. Fruit South (1988) 9(6): 5-7, 17.

Hightower, M. Backyard Vineyard a Lifeline for Southern Sensation Grape. University of Arkansas Division of Agriculture. (2022).

Scheiner, J. Southern Sensation Seedless: A New Table Grape for the Mid-South. University of Georgia. (2022) Southern Region Small Fruit Consortium 22(2). https://smallfruits.org/2022/04/southern-sensation-seedless-a-new-table-grape-for-the-mid-south/?cat=34.

* cited by examiner

*Primary Examiner* — Karen M Redden
(74) *Attorney, Agent, or Firm* — Quarles & Brady, LLP

(57) ABSTRACT

The new cultivar of grape originated from a hand-pollinated cross of 'Dunstan-210' (female parent, not patented) and 'Black Monukka' (male parent, not patented) made in 1970. The seedlings fruited in the summer of 1973 in a vineyard near Clarksville, Ark. and one was selected for its potential as a table grape for utilization in the southern United States. The original vine was tested as 'Ark. 1400'. The new cultivar of grapevine is a white, seedless table grape which provides advancements in Pierce's Disease tolerance (*Xylella fastidiosa* Wells et al.) for the southern region of the United States. This cultivar produces large, attractive fruit clusters with berries that have a neutral flavor and palatable, thin skin.

2 Drawing Sheets

Latin name: *Vitis* L. hybrid.
Varietal denomination: 'A-1400'.

BACKGROUND

The new and distinct grapevine named 'A-1400' is described herein. The new cultivar originated from a hand-pollinated cross of 'Dunstan-210' (female parent, non-patented) and 'Black Monukka' (male parent, non-patented) made in 1970. The seedlings fruited in the summer of 1973 in a vineyard near Clarksville, Ark. and one was selected for its potential as a table grape for utilization in the southern United States. The original vine was tested as 'A-1400'. The new cultivar of grapevine is a white, seedless table grape which provides advancements in Pierce's Disease tolerance (*Xylella fastidiosa* Wells et al.) for the southern region of the United States. 'A-1400' produces large, attractive fruit clusters with berries that have a neutral flavor and palatable, thin skin.

SUMMARY OF THE INVENTION

The new and distinct grapevine cultivar originated from a hand-pollinated cross of 'Dunstan-210' (female parent, non-patented) and 'Black Monukka' (male parent, non-patented) made in 1970 near Clarksville, Ark. The seeds resulting from this controlled hybridization were germinated in a greenhouse during the winter of 1970-71. Resulting seedlings were planted in the spring of 1971 in a vineyard near Clarksville, Ark. The seedlings fruited in the summer of 1973 and one seedling, designated Arkansas Selection 1400, and was selected for its potential for fresh-market production as a table grape.

During late 1973 and early 1974, the original plant selection was propagated asexually at the above-noted location, by rooting hardwood cuttings. A test planting of three vines was established. In all propagations, hardwood cuttings were used and the selection rooted readily from hardwood cuttings. All propagules (resulting plants) of the new cultivar have been observed to be true to type in that during all asexual multiplication, the vegetative and fruit characteristics of the original plant have been maintained. All vines planted from hardwood cutting propagation fruited in the second or third season of growth in the vineyard after planting.

Vines of the new cultivar have good growth, not being excessively vigorous and maintain good health throughout the growing season. Test plantings at two planting sites in Texas, Somerville, Tex. and Stephenville, Tex., have shown merit for use in the southern United States. 'A-1400' has produced well as grafted plants in tests conducted in Texas and has been evaluated on '1103 Paulsen' (non-patented) rootstock. Adaptation to the Texas test sites is good, with plants showing winter injury and heat damage to be minimal in these environments and resistance to Pierce's disease to be of value for the region.

The health of the new cultivar is good. Vines were evaluated for presence of the following diseases: powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopara viticola* Berl. & de Toni.), anthracnose (*Elsinoë ampelina* Shear), and black rot (*Guignardia bidwellii* Viala & Ravaz). The new cultivar appears to be less susceptible to downy mildew than 'Blanc Du Bois', though infection has been observed. Fungal disease can be controlled by the use of available fungicides. No symptoms of Pierce's Disease were observed at the test sites.

Average harvest date of this new cultivar in Texas is 16 July in Somerville, and 23 July in Stephenville. The berries are small-sized (ave. 2.3 g) and ellipsoid in shape. Fruit is seedless with small traces undetectable while eating. The flavor of the berry is neutral with balanced sweetness and acidity. Soluble solids average 16.0%. Fruit cracking and skin splitting is limited though some may be seen in severe rainfall pressure seasons. Clusters are medium, with tight cluster-fill. Average cluster weight was 306.4 g in Clarksville, Ark., 237.4 g in Somerville, Tex., and 575.5 g in Stephenville, Tex. Yield averages ranged from 5.5 kg/vine in Somerville, Tex. and 15.9 kg/vine in Stephenville, Tex.

The flavor attributes for the new cultivar are reflective of commercial standards for quality neutral table grapes.

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR

Figure 1:
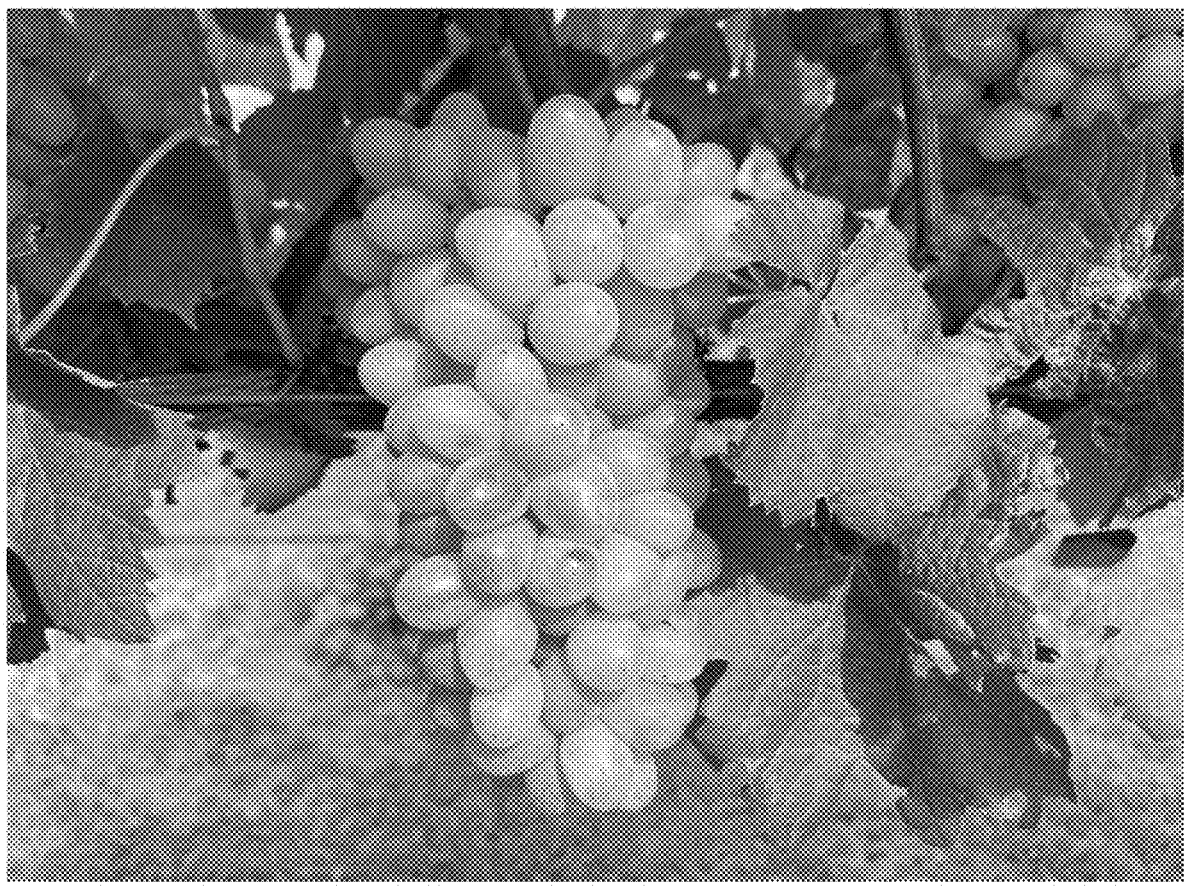
FIG. 1 is a photograph showing typical cluster of healthy fruit on a five-year-old vine, near Somerville, Tex.
Figure 2:
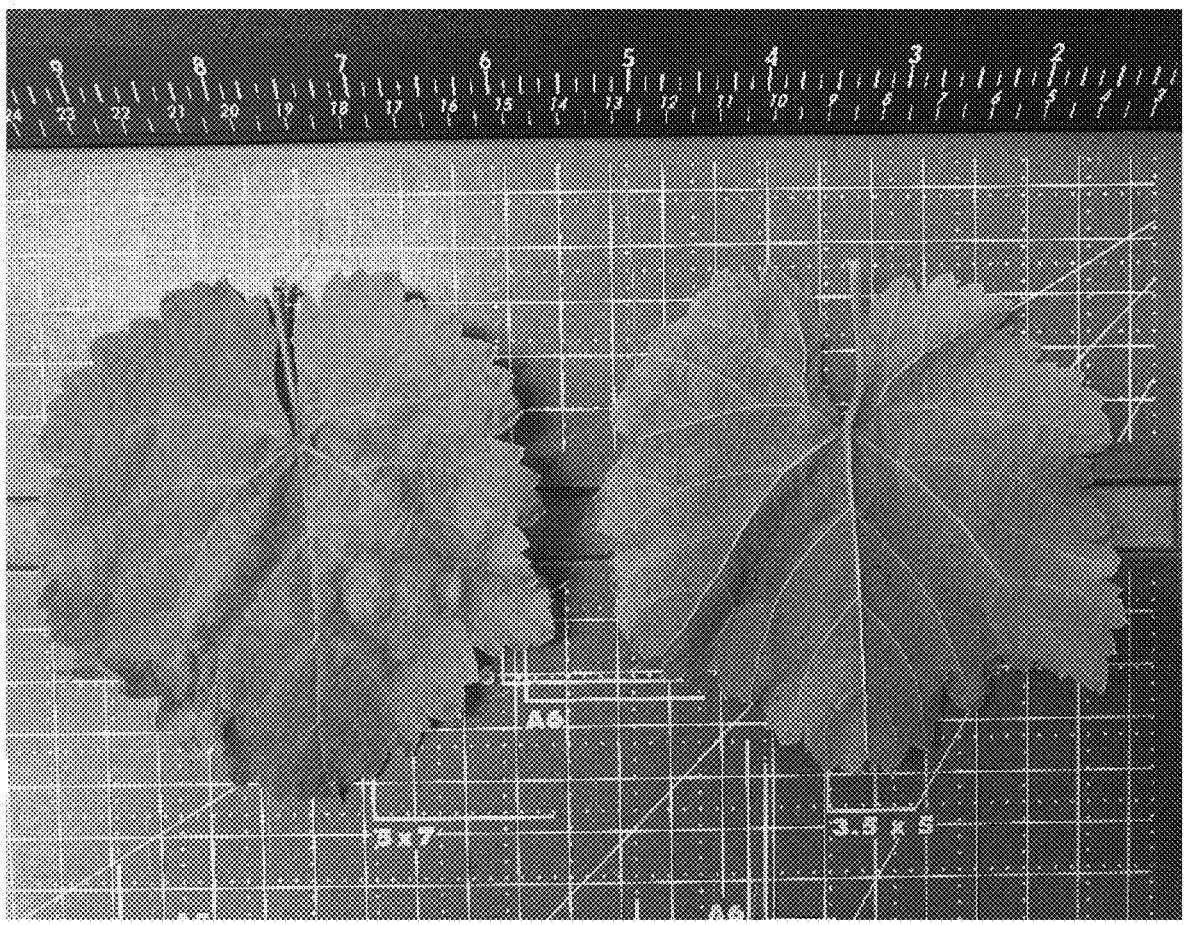
FIG. 2 is a photograph showing the leaf adaxial (left) and abaxial (right) view, near Somerville, Tex. Leaves were collected from a five-year-old vine.

'A-1400' differs from the female parent, 'Dunstan-210', in that 'A-1400' produces green-skinned and seedless fruit, in contrast to 'Dunstan-210' which is blue-skinned and seeded. 'A-1400' differs from the male parent 'Black Monukka'. 'A-1400' has green fruit skin as opposed to the dark purple to black fruit skin of 'Black Monukka'. 'A-1400' is unique from similar cultivars. The proposed variety blooms an average of 4 days earlier than 'Victoria Red' (non-patented variety). Berry weight of 'A-1400' averages 2.3 g, which is 4.6 g smaller than 'Victoria Red' (ave. 6.9 g). The pH juice of 'A-1400' is slightly higher than that of 'Victoria Red', measuring 3.96 and 3.84, respectively.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Somerville, Tex. Vines used for measurement were irrigated using trickle (drip) irrigation. Vines were fertilized annually in spring with Nitrogen or complete fertilizers. No shoot or leaf thinning practices were conducted on the vines.

Vine:

*Size*.—Evaluation vines are grown on a 1.5 m tall, single-wire trellis, bilateral cordon training system spaced 2.4 m between vines. Vines occupy this space fully.

*Growth vigor*.—Moderate, not excessive.

*Density of foliage*.—Moderate.

*Productivity*.—5.5 kg/vine in Somerville, Tex. and 15.9 kg/vine in Stephenville, Tex.

*Rootstock*.—'1103 Paulsen' at Somerville, Tex. and Stephenville, Tex.

*Cold hardiness*.—Hardy to −12.7° C. (9° F.); potentially hardier as this was the coldest temperature experienced at the test site.

Shoots (current-season canes):

*Color of shoots* (*current-season canes*).—Sun exposed surface: yellow-green group (144A); shaded surface: yellow-green group (144A); no presence of anthocyanin on any portion of the current season shoots.

*Shoot attitude*.—Upright.

*Openness of shoot tip*.—Half-open.

*Prostrate hairs on young shoot tip*.—Absent.

*Erect hairs on the internodes*.—Present, Medium density.

Canes (mature, dormant):

*Color of mature, dormant cane*.—Base: brown group (199A); midpoint: brown group (199A); terminal: brown group (199B); anthocyanin pigments are absent on mature canes.

*Texture of mature, dormant canes*.—Moderately rough-textured.

*Shape of dormant cane*.—Round.

*Length of mature, dormant canes*.—2.07 m.

*Diameter of mature, dormant cane*.—Base: 1.01 cm; midpoint: 0.81 cm; terminal: 0.15 cm.

*Internode length of mature, dormant canes*.—Base: 7.65 cm; midpoint: 5.07 cm; terminal: 2.21 cm.

*Lenticels*.—Absent.

*Maturity in the fall*.—Canes were mature to tips in the fall.

Trunk:

*Diameter at 30 cm above soil level.*—7.30 cm.

*Shape.*—Round to oval.

*Trunk straps.*—Present.

*Surface texture.*—Rough, with exfoliating bark.

*Color.*—Inner bark color: brown group (199A); outer bark color: brown group (199D).

Foliage:

*Arrangement of mature leaves.*—Simple.

*Shape of mature leaves.*—Lobed.

*Number of lobes on mature leaves.*—2 lobes.

*Petiole sinus of mature leaves.*—Slightly to wide open; depth: 3.15 cm; width: 0.94 cm.

*Venation of mature leaves.*—Reticulate.

*Teeth shape of mature leaves.*—Serrate, typically both sides of teeth convex.

*Size of teeth.*—Depth: 5.32 mm; width: 7.4 mm.

*Surface texture of mature leaves.*—Abaxial surface: smooth, no blistering; adaxial surface: smooth, no blistering.

*Dimensions of mature leaves.*—Length: 13.24 cm; width: 11.30 cm; thickness: <1.00 mm.

*Pubescence on mature leaves.*—Abaxial surface: none; adaxial surface: none; prostrate hairs between main veins: absent; amount of erect hairs on main veins: absent.

*Color of mature leaves.*—Base abaxial: green group (140B); base adaxial: yellow-green group (144D); midpoint abaxial: green group (140B); midpoint adaxial: yellow-green group (144D); terminal abaxial: yellow-green group (144D); terminal adaxial: yellow-green group (144D); no anthocyanin on any portion of mature leaves.

*Autumn coloration of mature leaves.*—Abaxial surface: yellow-green group (145B); adaxial surface: yellow-green group (145C); anthocyanins: absent.

*Color of veins on mature leaves.*—Abaxial surface: yellow-green group (150B); adaxial surface: yellow-green group (150B); no anthocyanins on any portion leaf veins.

*Leaf pubescence on young leaves.*—Abaxial surface: absent; adaxial surface: absent.

*Color of young leaves.*—Base abaxial: greyed-orange group (167A); base adaxial: greyed-orange group (167A); midpoint abaxial greyed-orange group (167A); midpoint adaxial: greyed-orange group (167A); terminal abaxial: greyed-orange group (167A); terminal adaxial: greyed-orange group (167A); anthocyanins present on leaves uniformly giving them orange tint described above: greyed-orange group (167A).

*Vein color of young leaves.*—Abaxial surface: yellow-green group (145B); adaxial surface: yellow-green group (145B).

*Texture of young leaf veins.*—Abaxial surface: smooth; adaxial surface: smooth.

Petioles:

*Color of mature petioles.*—Yellow-green group (145B); sun-exposed areas are greyed-red group (38D).

*Anthocyanin presence, mature petioles.*—Yes, on sun-exposed areas; color: red group (38D).

*Dimensions of mature petioles.*—Length: 5.52 cm; diameter: 1.30 mm.

*Color of young petioles.*—Yellow-green group (145B).

*Anthocyanin presence, young petioles.*—Absent.

*Dimensions of young petioles.*—Length: 2.59 cm; diameter: 0.17 mm.

Tendrils:

*First tendril found at node number.*—3 to 6.

*Orientation.*—Opposite.

*Dimensions.*—Length: 9.71 cm; diameter: 0.37 mm.

*Texture.*—Smooth, no pubescence present.

*Color of mature tendril.*—Yellow-green group (145B).

*Shape and tendency.*—Tendrils are forked and curl.

Buds:

*Number of buds on current, single-season cane.*—50.

*Dimensions of dormant buds.*—Diameter: 5.26 mm; length: 5.02 mm.

*Shape of dormant buds.*—Pyramidal to rounded pyramid (teardrop).

*Color of dormant buds.*—Brown group (199A).

*Texture of dormant buds.*—Smooth, no pubescence.

*Bud break.*—4 March, early.

Disease resistance:

*Vines were evaluated for presence of the following diseases.*—Powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopara viticola* Berl. & de Toni.), anthracnose (*Elsinoë ampelina* Shear), and black rot (*Guignardia bidwellii* Viala & Ravaz). Less susceptible to downy mildew than 'Blanc Du Bois'. Fungal disease can be controlled by the use of available fungicides. No symptoms of Pierce's Disease (*Xylella fastidiosa* Wells et al.) were experienced at either Texas location where Pierce's Disease is common.

Flower:

*Fragrance.*—Moderate.

*Sex.*—Perfect, hermaphrodite.

*Bloom dates.*—First bloom: 8 April; full bloom: 12 April; last bloom: 17 April.

*Flowers per cluster.*—321.

*Inflorescence dimensions.*—Length: 12.40 cm; diameter: 5.10 cm.

*Flower dimensions.*—Length: 6.58 mm; diameter: 6.58 mm.

*Flower longevity.*—<7 days, flowers mature and transition to fruit development quickly.

*Flower shape.*—Typical grape flower with calyptra, inconspicuous.

Stamens:

*Number.*—5.

*Color.*—Filament: yellow group (4D); anther: yellow group 4C.

Pistil:

*Number.*—1.

*Length.*—1.92 mm.

*Color.*—Yellow-green group (149C).

Pollen:

*Color.*—Yellow group 4C.

*Quantity.*—Moderate.

Petal:

*Number.*—6.

*Color.*—Yellow-green group (149C).

Sepals: Absent.

Pedicel:

*Dimensions*.—Length: 0.86 cm; diameter: 0.15 cm.

*Color*.—Yellow-green group (149C).

Fruit:

*Maturity*.—6 July.

*Berry shape*.—Ellipsoid.

*Berry color*.—Skin: yellow-green group (150A); flesh: yellow group (1D); anthocyanins: absent from flesh and skin.

*Berry dimensions*.—Diameter at equator: 1.85 cm; diameter at base: 1.65 cm; diameter at apex: 1.18 cm; length: 1.66 cm.

*Berry weight*.—2.30 g.

*Berry skin texture*.—Crisp, thin, non-slip.

*Firmness*.—Soft.

*Skin thickness*.—<1 mm.

*Tenacity*.—Moderate, does not rupture easily.

*Brush length*.—4.58 mm.

*Seeds*.—Considered seedless; small, rudimentary seed traces present but undetectable while eating.

*Juiciness*.—Moderate to high.

*Flavor*.—Neutral, good balance of sugar and acid.

Juice:

*Soluble solids*.—16.0%.

*Titratable acidity*.—4.61 g/L tartaric acid.

*ph*.—3.96.

*Color*.—Yellow-green group (149D).

Cluster:

*Weight*.—237.42 g.

*Cluster dimensions*.—Length: 23.10 cm; width: 10.00 cm.

*Berries per cluster*.—123.

*Cluster per vine*.—34.

*Clusters per shoot*.—2.

*Peduncle* (*primary*).—Length: 2.27 cm; diameter: 2.88 mm; color: yellow-green group (149C).

*Density*.—Dense.

Shipping quality:

*Keeping quality*.—Berry quality was maintained at 41° F. at 80-90% relative humidity for 21 days.

Use: Fresh market seedless table grape with good yield potential and tolerance to Pierce's disease adapted to the southern United States. This variety is intended for local market sales.

We claim:

1. A new and distinct cultivar of grapevine named 'A-1400' is substantially illustrated and described herein.

* * * * *